United States Patent
Zheng

(10) Patent No.: US 10,696,643 B2
(45) Date of Patent: Jun. 30, 2020

(54) POSACONAZOLE, COMPOSITION, INTERMEDIATE, PREPARATION METHOD AND USE THEREOF

(71) Applicant: Zhejiang Ausun Pharmaceutical Co., Ltd., Zhejiang (CN)

(72) Inventor: Zhiguo Zheng, Zhejiang (CN)

(73) Assignee: Zhejiang Ausun Pharmaceutical Co., Ltd., Zhejiang (CN)

( * ) Notice: Subject to any disclaimer, the term of this patent is extended or adjusted under 35 U.S.C. 154(b) by 10 days.

(21) Appl. No.: 16/081,551

(22) PCT Filed: Mar. 4, 2016

(86) PCT No.: PCT/CN2016/075594
§ 371 (c)(1),
(2) Date: Aug. 31, 2018

(87) PCT Pub. No.: WO2017/147893
PCT Pub. Date: Sep. 8, 2017

(65) Prior Publication Data
US 2019/0071408 A1   Mar. 7, 2019

(51) Int. Cl.
*C07D 263/26* (2006.01)
*C07D 405/14* (2006.01)
*C07D 405/06* (2006.01)
*C07D 413/06* (2006.01)
*C07D 407/06* (2006.01)

(52) U.S. Cl.
CPC ......... *C07D 263/26* (2013.01); *C07D 405/06* (2013.01); *C07D 405/14* (2013.01); *C07D 407/06* (2013.01); *C07D 413/06* (2013.01)

(58) Field of Classification Search
CPC .. C07D 263/26; C07D 405/06; C07D 405/14; C07D 407/06; C07D 413/06
See application file for complete search history.

(56) References Cited

U.S. PATENT DOCUMENTS

2012/0029230 A1   2/2012  Kuo et al.

FOREIGN PATENT DOCUMENTS

| CN | 1122134 A | 5/1996 |
|---|---|---|
| CN | 101824009 A | 9/2010 |
| CN | 105503765 A | 4/2016 |
| WO | WO-2009/141837 A2 | 11/2009 |
| WO | WO-2013/042138 A2 | 3/2013 |

OTHER PUBLICATIONS

Lelais et al. "Synthesis of new β-amino acids and novel β-peptides, and structural investigations." ETH Zurich Research Collection, 2004.
Bates et al, "Diastereoselective Cobalt-mediated Acylation-Cyclization of Allenes." Synlett, No. 4, pp. 532-534, 2001.
Jurberg et al, "Hydroalkylatino of Alkynyl Ethers via a Gold(I)-Catalyzed 1,5-Hydride Shift/Cyclization Sequence." JACS Articles, J. Am. Chem. Soc., 132, 3543-3552, 3543, Published on Web Feb. 12, 2010.
Sebesta et al, "Preparation of (S,S)-Fmoc-β²hIle-OH, (S)-Fmoc-β²hMet-OH, and (S)-Fmoc-β²hTyr(ᵗBu)-OH for Solid-Phase Syntheses of β²- and β²/β³-Peptides." Helvetica Chimica Acta, vol. 86, pp. 4061-4072, 2003.
First Office Action Issued in Chinese Patent Application No. 201410505311.3; Publication No. CN 105503765 A, dated Jul. 20, 2017.
Ke et al "Catalytic Asymmetric Bromoetherification and Desymmetrization of Olefinic 1,3-Diols with C₂-Symmetric Sulfides" Journal of the American Chemical Society vol. 136, pp. 5627-2630, 2014.
Hintermann et al "A Useful Modification of the Evans Auxiliary: 4-Isopropyl-5,5-Diphenyloxazolidin-2-One" Helvetica Chimica Acta vol. 81, pp. 2093-2126, 1998.
Lelais et al "Preparation of Protected 132- and (33-Homocysteine, 132- and I33-Homohistidine, and 132-Homoserine for Solid-Phase Syntheses" Helvetica Chimica Acta vol. 87, pp. 3131-3159, 2004.
Scharnagel et al "The First Modular Route to Core-Chiral Bispidine Ligands and Their Application in Enantioselective Copper(II)-Catalyzed Henry Reactions" Chemistry A European Journal vol. 21, pp. 12488-12500, 2015.
Seebach et al "Enantioselective Preparation of 2-Aminomethyl Carboxylic Acid Derivatives: Solving the [32-Amino Acid Problem with the Chiral Auxiliary 4-Isopropyl-5,5-Diphenyloxazolidin-2-One (Dioz)" Helvetica Chimica Acta vol. 86, pp. 1852-1861, 2003.
Yoshida et al "Development of a Practical and Scalable Synthesis of (R)- and (S)-3-Amino-2-[(Benzyloxyl)Methyl]Propan-1-Ol Monohydrochloride: A Useful C-4 Chiral Building Block" Organic Process Research and Development vol. 16, pp. 1527-1537, 2012.
Partial Search Report Issued in European Patent Application No. 16 892 084.1 dated Jun. 13, 2019.
Notice of Reasons for Rejection Issued in Japanese Patent Application No. 2018-565,443 dated Jul. 9, 2019.
Extended Search Report Issued in European Patent Application No. 16 892 084.1 dated Sep. 30, 2019.

*Primary Examiner* — Joseph R Kosack
(74) *Attorney, Agent, or Firm* — Cesari and McKenna, LLP

(57) ABSTRACT

The present invention relates to a compound of formula III, wherein, R is selected from the group consisting of $C_1$-$C_4$ alkyl, substituted or unsubstituted phenyl, and substituted or unsubstituted benzyl, preferably isopropyl; and two Ar groups may be the same or different, and are each independently selected from the group consisting of substituted or unsubstituted aryl groups, preferably substituted or unsubstituted phenyl, such as p-methoxyphenyl and the like, wherein the compound is preferably in a solid form.

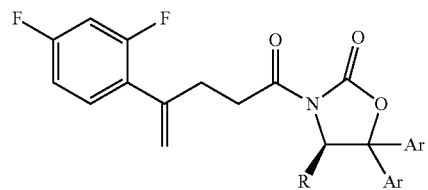

Formula III

15 Claims, 1 Drawing Sheet

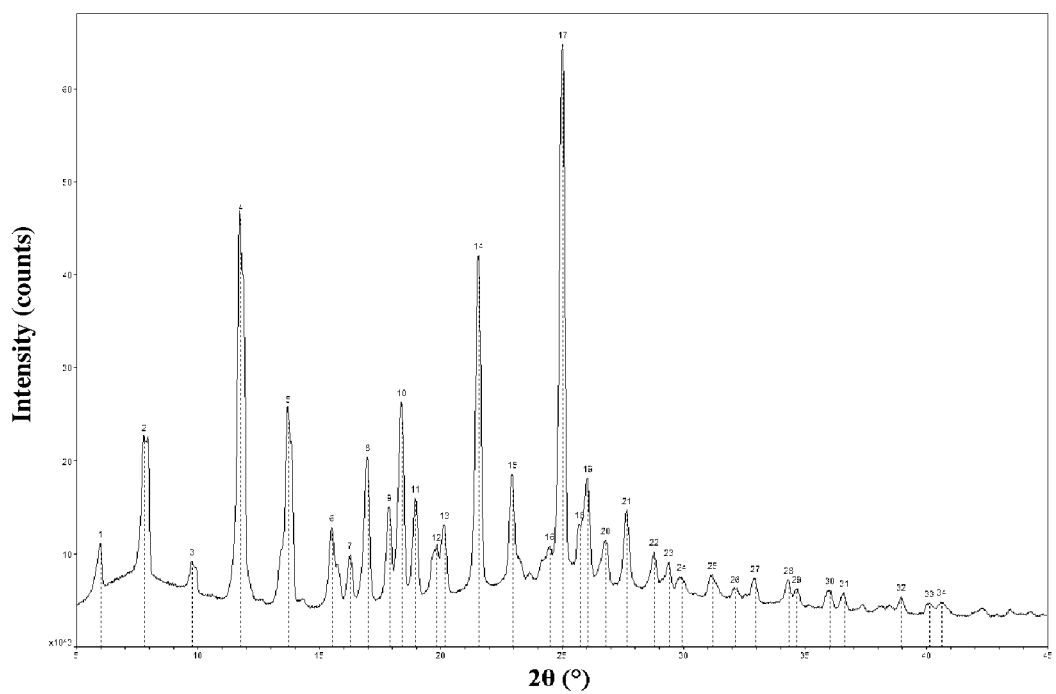

POSACONAZOLE, COMPOSITION, INTERMEDIATE, PREPARATION METHOD AND USE THEREOF

CROSS-REFERENCE TO RELATED APPLICATIONS

This application is the National Stage of International Application No. PCT/CN2016/075594, filed Mar. 4, 2016. The content of this application is hereby incorporated by reference in its entirety.

TECHNICAL FIELD

The present invention relates to medical technical field, and particularly to posaconazole, a composition, and an intermediate, a synthesis method and use in synthesizing posaconazole thereof.

BACKGROUND

Posaconazole (CAS Registration No: 171228-49-2; CAS name: 2,5-anhydro-1,3,4-trideoxy-2-C-(2,4-difluorophenyl)-4-[[4-[4-[1-(1S,2S)-1-ethyl-2-hydroxypropyl]-1,5-dihydro-5-oxo-4H-1,2,4-triazol-4-yl]phenyl]-1-piperazinyl]phenoxy[methyl]-1-(1H-1,2,4-triazol-1-yl)-D-threopentitol) is used for preventing and treating invasive fungal infections, such as those which are drug resistant or to which other medicines are ineffective, and the structure thereof is as follows:

Formula I wherein Q is substituted or unsubstituted phenylsulfonyl, p-tosylsulfonyl, p-chlorophenylsulfonyl or the like. U.S. Pat. No. 5,403,937A reported the synthesis of this intermediate (FIG. 1),

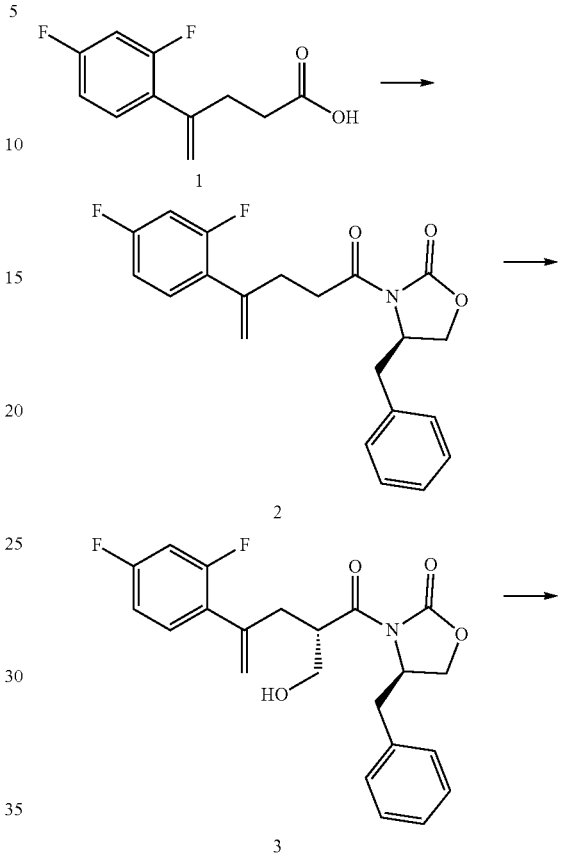

One important intermediate for preparing posaconazole is a compound of formula IX, Formula IX

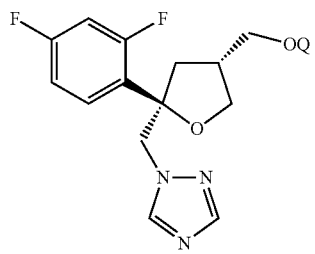

-continued

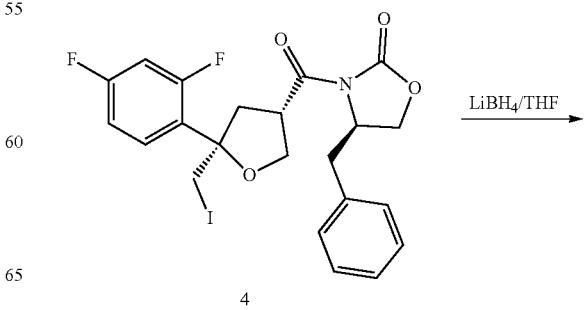

LiBH$_4$/THF

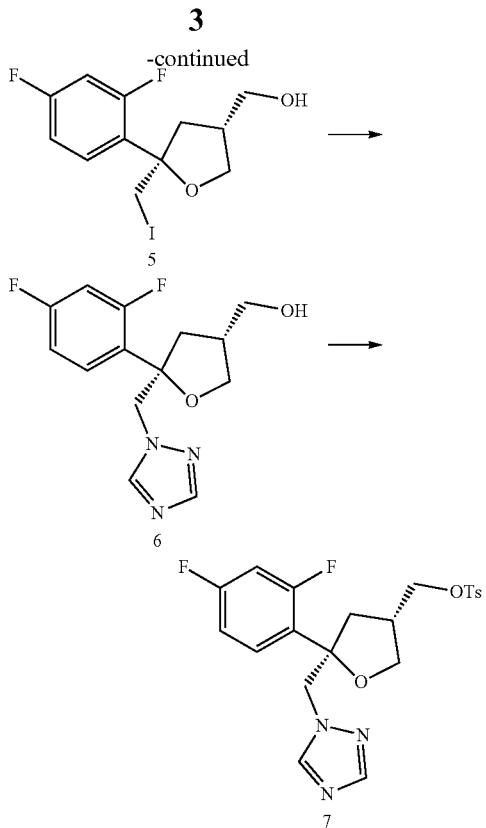

characterized in that, compound (2), obtained by reacting acid (1) with R-4-benzyl oxazolidone as a chiral auxiliary, is subjected to an asymmetric hydroxy-methylenation with triformol mediated by triethylamine and titanium tetrachloride to obtain compound (3), the compound (3) is then subjected to an intra-molecular iodization and etherification reaction to stereoselectively obtain tetrahydrofuran intermediate (4) (with a cis/trans molar ratio of 85:15 to 95:5), which is then reduced by lithium borohydride to remove the chiral auxiliary to obtain iodohydrin intermediate (5). The intermediates in all steps of the process are oily materials. In particular, an excess amount of iodine is required in the step of the intra-molecular iodo-ether cyclization, which is expensive and highly toxic. Furthermore, for removing the chiral auxiliary with lithium borohydride, not only the reagent is expensive, but also the iodohydrin intermediate (5) obtained after reduction is required to be separated from the chiral auxiliary by column chromatography, unfavorable for industrial production.

WO2013042138 reported another synthesis method of a compound of formula X (FIG. 2),

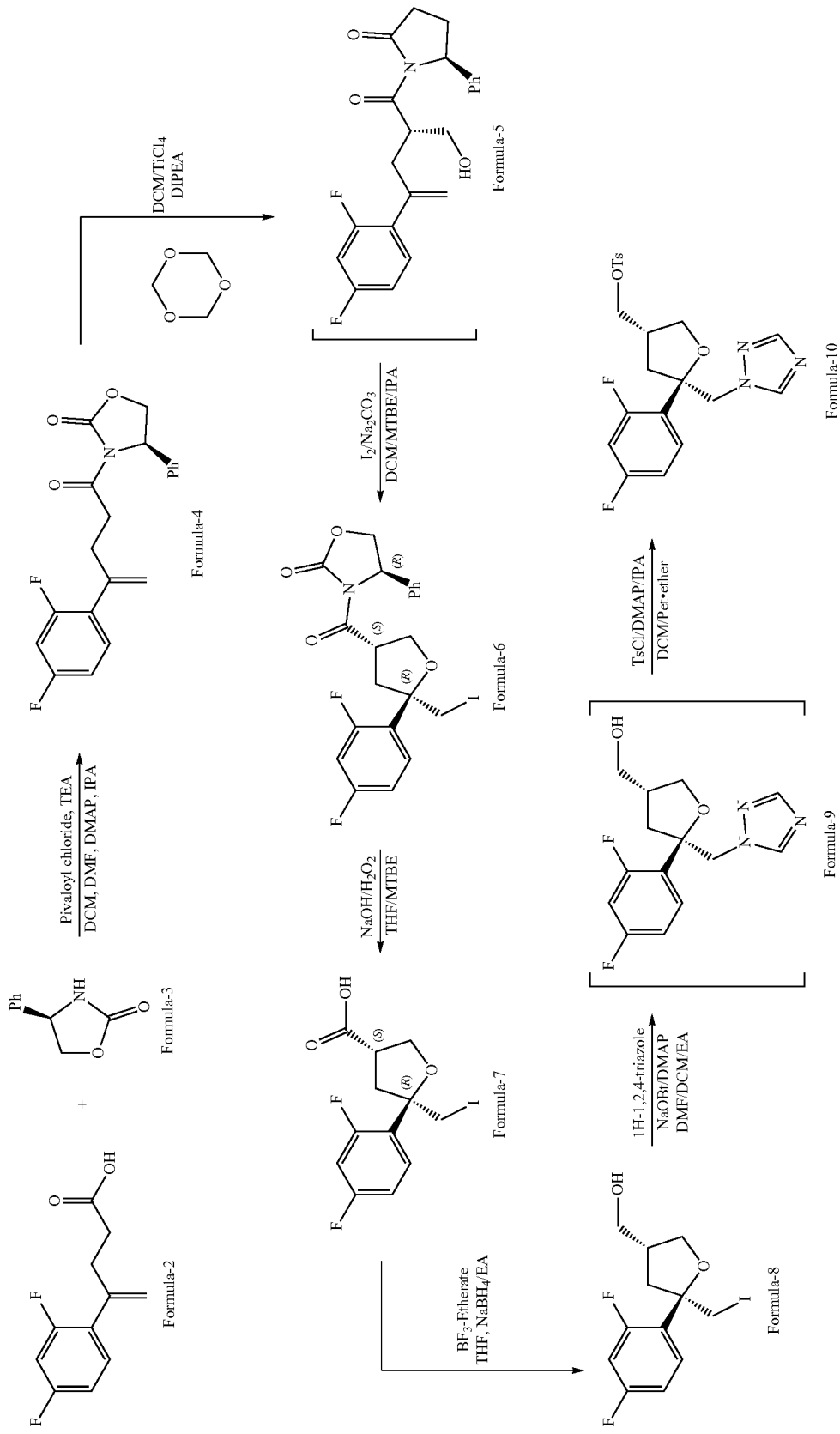

characterized in that, R-4-phenyl oxazolidone is used as a chiral auxiliary, and the auxiliary is removed by hydrolyzing with sodium hydroxide and hydrogen peroxide. Although this route avoids separating the obtained iodo acid intermediate (formula-7) and the chiral auxiliary by a column chromatography, it is still required to use an excess amount of iodine in the step of preparing the compound of formula-6 by iodization and cyclization, which confronts with the same problem as the above patent application. Furthermore, because hydrogen peroxide is required to be used in the step of removing the auxiliary by hydrolyzing with sodium hydroxide, there is a risk in industrial production.

SUMMARY

In order to solve the above problems, after intensive research, the inventors find that the use of a chiral auxiliary having a structure of formula II allows the key intermediate to be crystalized more easily. This facilitates the purification, avoids using an excess amount of halogen in the halogenation and cyclization step, and avoids using hydrogen peroxide which may bring potential safety hazard in industry in the hydrolyzation removal of the auxiliary, which allows the auxiliary and solvent to be recovered more safely, thereby reducing the production cost. As a result, the present invention is achieved.

The technical solutions of the present invention comprise, but are not limited to, the following ones.

Technical solution 1: A compound of formula II,

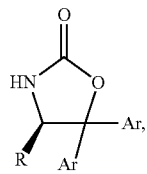

Formula II wherein,

R is selected from the group consisting of $C_1$-$C_4$ alkyl, substituted or unsubstituted phenyl, and substituted or unsubstituted benzyl, preferably isopropyl; and two Ar groups may be the same or different, and are each independently selected from the group consisting of substituted or unsubstituted aryl groups, preferably substituted or unsubstituted phenyl, such as p-methoxyphenyl.

Technical solution 2: A compound of formula III,

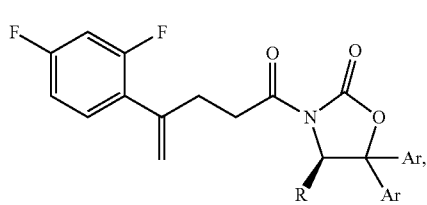

Formula III wherein,

R and Ar are as defined above.

Technical solution 3: A compound of formula IV,

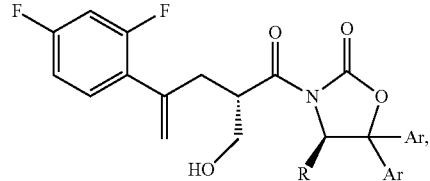

IV wherein,

R and Ar are as defined above, wherein the compound is preferably in a solid form.

Technical solution 4: A compound of formula V,

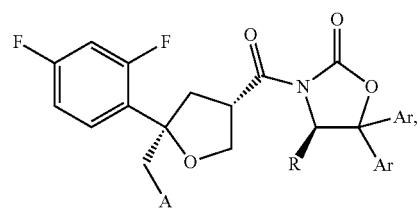

V wherein,

R and Ar are as defined above; and

A is Br, Cl or I, preferably Br, wherein the compound is preferably in a solid form.

Technical solution 5: A compound of formula VI,

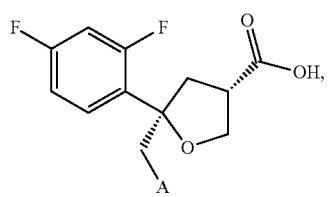

VI wherein,

A is selected from Cl or Br, preferably Br, wherein the compound is preferably in a solid form.

Technical solution 6: A compound of formula VII,

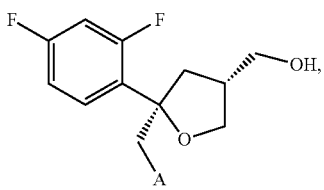

VII wherein,

A is selected from Cl or Br, preferably Br, wherein the compound is preferably in a solid form.

Technical solution 7: A composition comprising a compound of formula IX

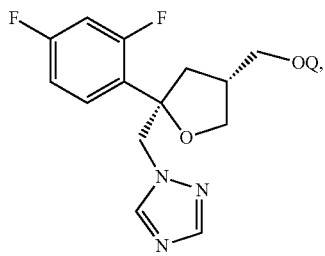

wherein,

Q is selected from substituted or unsubstituted phenylsulfonyl, preferably p-tosylsulfonyl or p-chlorophenylsulfonyl;

and a compound of formula X,

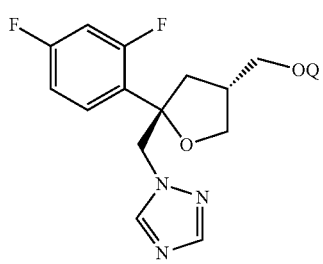

wherein, with respect to a total mass of the composition, a mass percentage of the compound of formula IX is 95% to 100%, and a mass percentage of the compound of formula X is 0% to 5.0%, and wherein the composition is preferably in a solid form.

Technical solution 14: A method for preparing a compound of formula III,

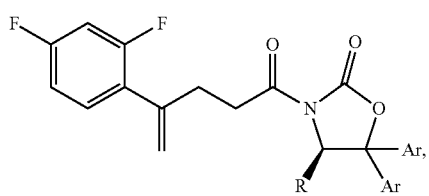

comprising:

subjecting a compound of formula I and a compound of formula II to an acylation reaction,

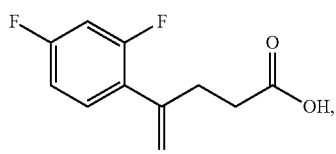

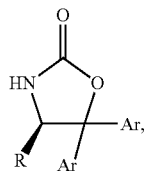

wherein,

R and Ar are as defined above.

Technical solution 15: The method of technical solution 14, wherein one or more acylating agents selected from the group consisting of oxalyl chloride, pivaloyl chloride, thionyl chloride, $POCl_3$, $PCl_3$, and $PCl_5$, preferably oxalyl chloride, thionyl chloride or pivaloyl chloride, are used in the acylation reaction.

Technical solution 16: The method of technical solution 14, wherein the acylation reaction is carried out in the presence of one or more bases selected from the group consisting of organometallic reagents such as butyl lithium and lithium diisopropylamide, or a mixture of an organic tertiary amine (such as triethylamine, diisopropylethylamine, pyridine, 4-dimethylaminopyridine, and N-methylmorpholine) and anhydrous lithium chloride.

Technical solution 17: The method of technical solution 14, wherein the acylation reaction is preferably carried out in the presence of butyl lithium, or pivaloyl chloride and a mixture of triethylamine and anhydrous lithium chloride.

Technical solution 18: The method of technical solution 14, wherein the acylation reaction is carried out in the presence of a polar aprotic solvent such as a chlorine-containing solvent and an ether solvent, preferably one or a mixture of tetrahydrofuran and dichloromethane.

Technical solution 19: A method for preparing a compound of formula IV,

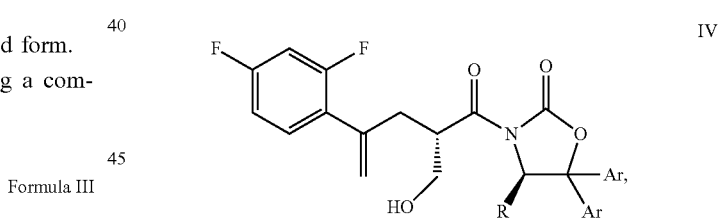

comprising:

subjecting a compound of formula III to a hydroxy methylenation with triformol,

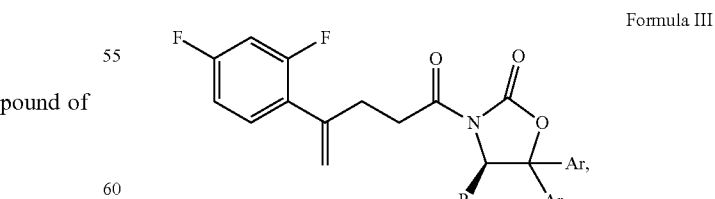

wherein,

R is selected from the group consisting of $C_1$-$C_4$ alkyl, substituted or unsubstituted phenyl, and substituted or unsubstituted benzyl, preferably isopropyl; and Ar is selected from substituted or unsubstituted phenyl, such as p-methoxyphenyl.

Technical solution 20: The method according to technical solution 19, wherein the hydroxy methylenation is carried out under an action of an organic base and titanium tetrachloride.

Technical solution 21: The method according to technical solution 20, wherein the organic base is one or more selected from the group consisting of organic tertiary amines, such as triethylamine, tri(tert-butyl)amine, N-methylmorpholine, and diisopropylethylamine, preferably triethylamine or diisopropylethylamine.

Technical solution 22: The method according to technical solution 19, wherein the hydroxy methylenation is carried out in one or more solvents selected from the group consisting of aprotic solvents such as a chlorine-containing solvent, an ester solvent, and an ether solvent, preferably dichloromethane or 1,2-dichloroethane.

Technical solution 23: A method for preparing a compound of formula V,

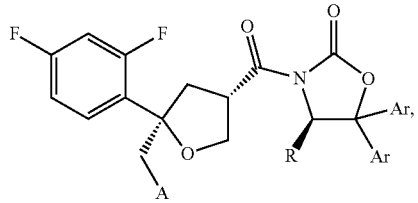

comprising:
reacting a compound of formula IV with a halogenating agent,

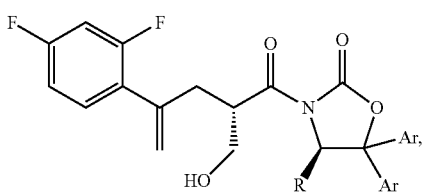

wherein,
R and Ar are as defined above; and
A is Br, Cl or I.

Technical solution 24: The method of technical solution 23, wherein the reaction is carried out under a neutral or alkaline condition.

Technical solution 25: The method of technical solution 23, wherein the halogenating agent comprises one or more selected from the group consisting of halogen, dihalohydantoin, N-bromosuccinimide (NBS), N-iodosuccinimide (NIS), and N-chlorosuccinimide (NCS), preferably iodine, NIS bromine, NBS or dibromo-hydantoin.

Technical solution 26: The method of technical solution 23, wherein the reaction is carried out in the presence of one or more bases selected from the group consisting of alkali metal hydroxides, metal carbonates, and metal bicarbonates, preferably sodium bicarbonate.

Technical solution 27: The method of technical solution 23, wherein the reaction is carried out in one or more solvents selected from the group consisting of polar aprotic solvents such as tetrahydrofuran, acetonitrile, and ethyl acetate, and protic solvents such as water and alcohol solvents, preferably a mixture of tetrahydrofuran and water.

Technical solution 28: A method for preparing a compound of formula VI,

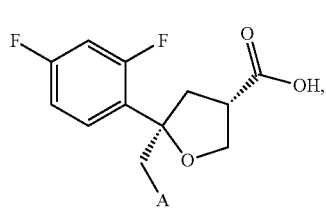

comprising:
hydrolyzing a compound of formula V,

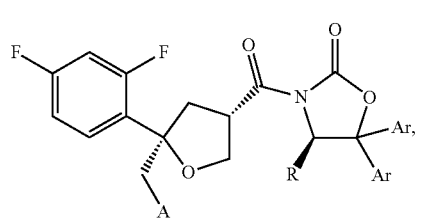

wherein,
R and Ar are as defined above; and
A is Br, Cl or I.

Technical solution 29: The method according to technical solution 28, wherein the hydrolyzation is carried out under an alkaline condition.

Technical solution 30: The method according to technical solution 28, wherein the hydrolyzation is carried out in the presence of one or more bases selected from the group consisting of alkali metal hydroxides and metal carbonates, preferably sodium hydroxide.

Technical solution 31: The method according to technical solution 28, wherein the hydrolyzation is carried out in one or more solvents selected from the group consisting of a mixture of an organic polar protic or aprotic solvent and water, preferably tetrahydrofuran and water.

Technical solution 32: A method for preparing a compound of formula VII,

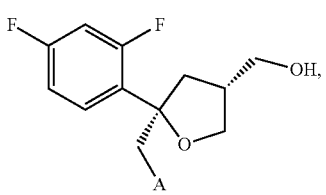

comprising:
reducing a compound of formula V,

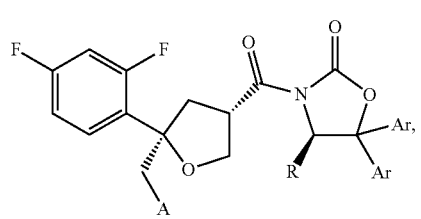

wherein,

R is selected from the group consisting of $C_1$-$C_4$ alkyl, substituted or unsubstituted phenyl, and substituted or unsubstituted benzyl, preferably isopropyl;

Ar is selected from substituted or unsubstituted phenyl, such as p-methoxyphenyl, and A is Br, Cl or I.

Technical solution 33: The method of technical solution 32, wherein one or more reducing agents selected from the group consisting of hydride reducing agents, preferably lithium borohydride, are used in the reduction-hydrogenation.

Technical solution 34: The method of technical solution 32, wherein the reduction is carried out in one or more solvents selected from the group consisting of methanol, ethanol, isopropanol, tetrahydrofuran, 2-methyltetrahydrofuran, dichloromethane and ethyl acetate.

Technical solution 35: A method for preparing a compound of formula VII,

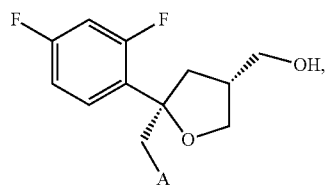

VII comprising:

reducing a compound of formula VI,

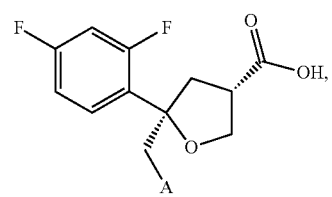

VI wherein,

A is Br or Cl.

Technical solution 36: The method of technical solution 35, wherein one or more reducing agents selected from the group consisting of diisobutylaluminum hydride, sodium borohydride, lithium borohydride, sodium borohydride/$BF_3$-diethyl ether, sodium aluminum bis(dihydride), sodium borohydride/aluminum chloride or borane/aluminum chloride, sodium borohydride/iodine and vitride solution are used in the reduction.

Technical solution 37: The method of technical solution 35, wherein the reduction is carried out in one or more solvents selected from the group consisting of organic polar aprotic solvents, such as tetrahydrofuran, toluene and dichloromethane, preferably tetrahydrofuran or toluene.

Technical solution 38: A method for preparing a compound of formula IX,

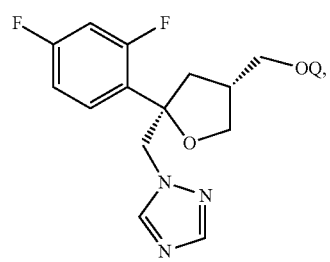

IX comprising the steps of:

g) reacting a compound of formula VII with 1,2,3-triazole alkali metal salt or 1,2,3-triazole,

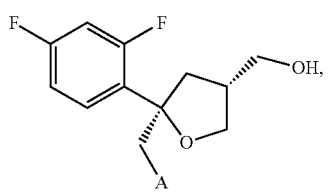

VII to produce a compound of formula VIII.

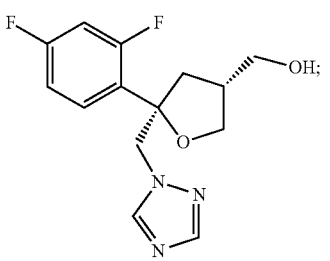

VIII and f) sulfonylating the compound of formula VIII;

wherein,

Q is selected from substituted or unsubstituted phenylsulfonyl, preferably p-tosylsulfonyl or p-chlorophenylsulfonyl;

A is Br; and the method further optionally comprises the step of:

preparing a compound of formula VII according to the method of any one of technical solutions 32 to 37.

Technical solution 39: The method of technical solution 38, wherein the step g) is carried out in the presence of one or more bases selected from the group consisting of metal hydroxides, metal alkoxides, and metal carbonates, such as NaH, KH, sodium alkoxide, $Na_2CO_3$, and $K_2CO_3$.

Technical solution 40: The method of technical solution 38, wherein the step g) is carried out in the presence of one or more catalysts selected from the group consisting of crown ethers such as 15-crown-5 and 18-crown-6, tetrabutylammonium iodide, a catalytic amount of KI or NaI.

Technical solution 41: The method of technical solution 38, wherein the step g) is carried out in one or more solvents selected from the group consisting of dipolar aprotic solvents, such as dimethylsulfoxide, N,N-dimethylformamide, N,N-dimethylacetamide, and N-methylpyrrolidinone.

Technical solution 42: The method of technical solution 38, wherein QX is used as a sulfonylating agent for the sulfonylation, wherein, Q is selected from substituted or unsubstituted phenylsulfonyl, preferably p-tosylsulfonyl or p-chlorophenylsulfonyl; and X is Br, Cl or I.

Technical solution 43: the method of technical solution 38, wherein the sulfonylation is carried out in the presence of one or more bases selected from the group consisting of organic bases, such as triethylamine, tributylamine, 4-dimethylaminopyridine, N-methylmorpholine, and diisopropylethylamine, preferably diisopropylethylamine Technical solution 44: the method of technical solution 38, wherein the sulfonylation is carried out in one or more solvents selected from the group consisting of chlorinated solvents and hydrocarbon solvents, preferably dichloromethane, toluene, or tetrahydrofuran.

Technical solution 45: A method for preparing a composition comprising a compound of formula IX,

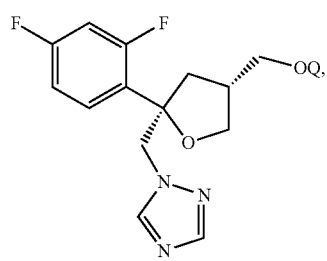

comprising the steps of:

g) reacting a compound of formula VII with 1,2,3-triazole alkali metal salt or 1,2,3-triazole,

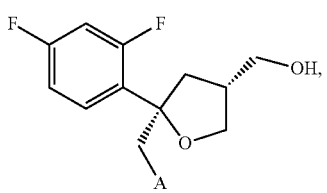

wherein,

A is Br, Cl or I, to produce a compound of formula VIII.

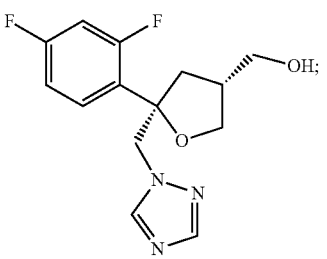

and f) sulfonylating the compound of formula VIII;
g) performing a recrystallization;

to obtain a composition comprising the compound of formula IX and a compound of formula X,

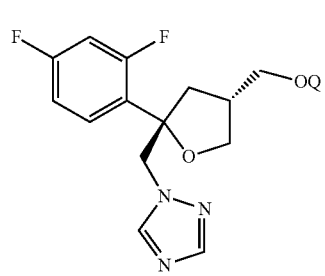

wherein, with respect to a total mass of the composition, a mass percentage of the compound of formula IX is 95% to 100%, and a mass percentage of the compound of formula X is 0% to 5.0%, and wherein the composition is preferably in a solid form.

Technical solution 46: The method of technical solution 45, wherein the step g) is carried out in the presence of one or more bases selected from the group consisting of metal hydroxides, metal alkoxides, and metal carbonates, such as NaH, KH, sodium alkoxide, $Na_2CO_3$, and $K_2CO_3$.

Technical solution 47: The method of technical solution 45, wherein A is Cl or Br, and the step g) is carried out in the presence of one or more catalysts selected from the group consisting of crown ethers such as 15-crown-5 and 18-crown-6, tetrabutylammonium iodide, a catalytic amount of KI or NaI.

Technical solution 48: The method of technical solution 45, wherein the step g) is carried out in one or more solvents selected from the group consisting of dipolar aprotic solvents, such as dimethylsulfoxide, N,N-dimethylformamide, N,N-dimethylacetamide, and N-methylpyrrolidinone.

Technical solution 49: The method of technical solution 45, wherein QX is used as a sulfonylating agent for the sulfonylation, wherein, Q is selected from substituted or unsubstituted phenylsulfonyl, preferably p-tosylsulfonyl or p-chlorophenylsulfonyl; and X is Br, Cl or I.

Technical solution 50: the method of technical solution 45, wherein the sulfonylation is carried out in the presence of one or more bases selected from the group consisting of organic bases, such as triethylamine, tributylamine, 4-dimethylaminopyridine, N-methylmorpholine, and diisopropylethylamine, preferably diisopropylethylamine Technical solution 51: the method of technical solution 45, wherein the sulfonylation is carried out in one or more solvents selected from the group consisting of chlorinated solvents and hydrocarbon solvents, preferably dichloromethane, toluene, or tetrahydrofuran.

Technical solution 52: The method of any one of technical solutions 14 to 18, wherein the compound of formula II is prepared by the method of any one of technical solutions 8 to 13.

Technical solution 53: The method of any one of technical solutions 19 to 22, wherein the compound of formula III is prepared by the method of any one of technical solutions 14 to 18 and 52.

Technical solution 54: The method of any one of technical solutions 23 to 27, wherein the compound of formula IV is prepared by the method of any one of technical solutions 19 to 22 and 53.

Technical solution 55: The method of any one of technical solutions 28 to 31, wherein the compound of formula V is prepared by the method of any one of technical solutions 23 to 27 and 54.

Technical solution 56: The method of any one of technical solutions 32 to 34, wherein the compound of formula V is prepared by the method of any one of technical solutions 23 to 27 and 54.

Technical solution 57: The method of any one of technical solutions 35 to 37, wherein the compound of formula VI is prepared by the method of any one of technical solutions 28 to 31 and 55.

Technical solution 58: The method of any one of technical solutions 38 to 44, wherein the compound of formula VII is prepared by the method of technical solution 56 or 57.

Technical solution 59: The method of any one of technical solutions 45 to 51, wherein the compound of formula VII is prepared by the method of any one of technical solutions 32 to 37 and 56 to 57.

Technical solution 60: The compound of technical solution 1 prepared by the method of any one of technical solutions 8 to 13.

Technical solution 61: The compound of technical solution 2 prepared by the method of any one of technical solutions 14 to 18 and 52.

Technical solution 62: The compound of technical solution 3 prepared by the method of any one of technical solutions 19 to 22 and 53.

Technical solution 63: The compound of technical solution 4 prepared by the method of any one of technical solutions 23 to 27 and 54.

Technical solution 64: The compound of technical solution 5 prepared by the method of any one of technical solutions 28 to 31 and 55.

Technical solution 65: The compound of technical solution 6 prepared by the method of any one of technical solutions 32 to 37 and 56 to 57.

Technical solution 66: A compound of formula IX,

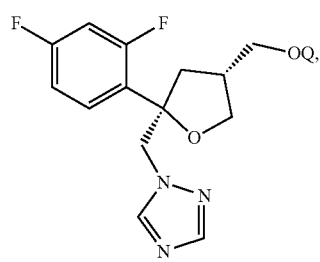

IX wherein,

Q is selected from substituted or unsubstituted phenylsulfonyl, preferably p-tosylsulfonyl or p-chlorophenylsulfonyl; and the compound of formula IX is prepared by the method of any one of technical solutions 38 to 44 and 58.

Technical solution 67: The solid state composition of technical solution 7 prepared by the method of any one of technical solutions 45 to 51 and 59.

Technical solution 68: Use of the compound of any one of technical solutions 1 to 6 and 60 to 66 or the composition of technical solution 7 or 67 in synthesizing posaconazole.

Technical solution 69: The compound of any one of technical solutions 1 to 6 and 60 to 66 or the composition of technical solution 7 or 67 used for synthesizing posaconazole.

Technical solution 70: A method for synthesizing posaconazole, comprising a step of preparing the compound of technical solution 1 by the method of any one of technical solutions 8 to 13.

Technical solution 71: A method for synthesizing posaconazole, comprising a step of preparing the compound of technical solution 2 by the method of any one of technical solutions 14 to 18 and 52.

Technical solution 72: A method for synthesizing posaconazole, comprising a step of preparing the compound of technical solution 3 by the method of any one of technical solutions 19 to 22 and 53.

Technical solution 73: A method for synthesizing posaconazole, comprising a step of preparing the compound of technical solution 4 by the method of any one of technical solutions 23 to 27 and 54.

Technical solution 74: A method for synthesizing posaconazole, comprising a step of preparing the compound of technical solution 5 by the method of any one of technical solutions 28 to 31 and 55.

Technical solution 75: A method for synthesizing posaconazole, comprising a step of preparing the compound of technical solution 6 by the method of any one of technical solutions 32 to 37 and 56 to 57.

Technical solution 76: A method for synthesizing posaconazole, comprising a step of preparing a compound of formula IX by the method of any one of technical solutions 38 to 44 and 58.

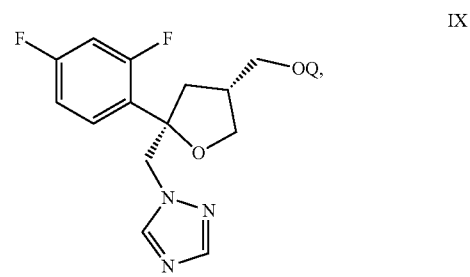

IX wherein,

Q is selected from substituted or unsubstituted phenylsulfonyl, preferably p-tosylsulfonyl or p-chlorophenylsulfonyl.

Technical solution 77: A method for synthesizing posaconazole, comprising a step of preparing the solid state composition of technical solution 7 by the method of any one of technical solutions 45 to 51 and 59.

Technical solution 78: A composition comprising posaconazole prepared from the solid state composition of technical solution 7.

Technical solution 79: The method for synthesizing posaconazole of any one of technical solutions 70 to 77, comprising the steps of:

reacting a compound of formula IX with a compound of formula A,

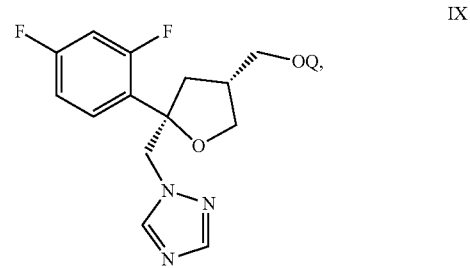

IX

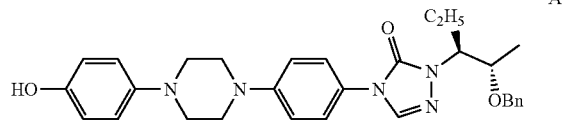

A wherein,

Q is selected from substituted or unsubstituted phenylsulfonyl, preferably p-tosylsulfonyl or p-chlorophenylsulfonyl;

to produce a compound of formula B,

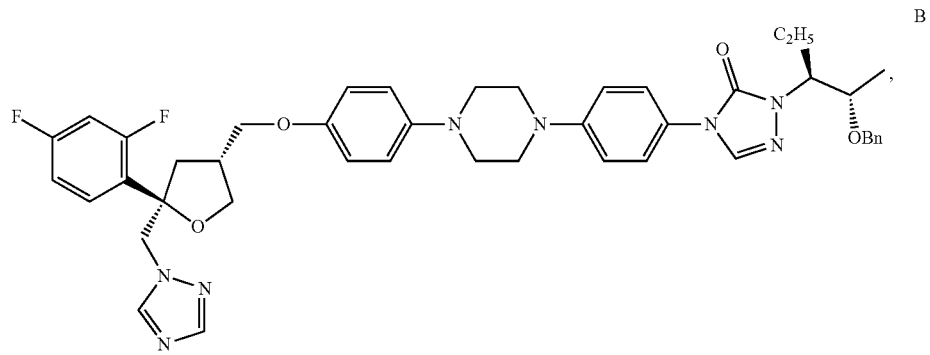 [SMILES: CC[C@@H]([C@H](C)OCc1ccccc1)n1ncn(-c2ccc(N3CCN(c4ccc(OC[C@@H]5CO[C@@](Cn6cncn6)(c6ccc(F)cc6F)C5)cc4)CC3)cc2)c1=O]

and hydrolyzing the compound of formula B into posaconazole.

Technical solution 80: A polymorph N of a compound of formula S,

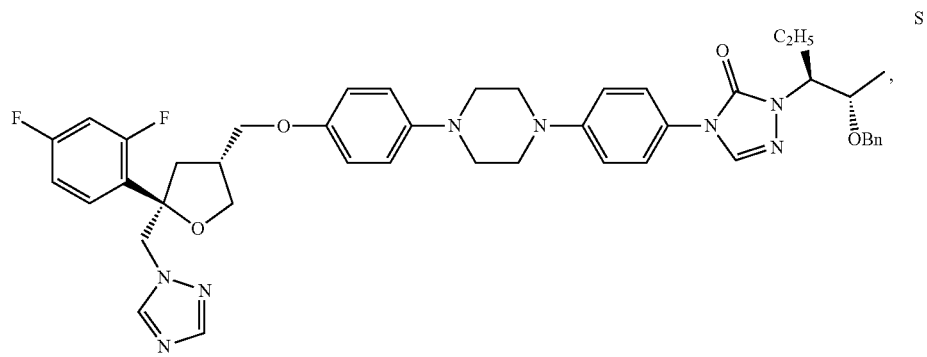 [SMILES: CC[C@@H]([C@H](C)OCc1ccccc1)n1ncn(-c2ccc(N3CCN(c4ccc(OC[C@@H]5CO[C@@](Cn6cncn6)(c6ccc(F)cc6F)C5)cc4)CC3)cc2)c1=O]

wherein the polymorph N has an XRD spectrum as shown in FIG. 1.

Technical solution 81: The polymorph N of the compound of formula S of technical solution 80 prepared by the method of any one of technical solutions 70 to 77 and 79.

Technical solution 82: Use of the compound of any one of technical solutions 1 to 6 and 60 to 66, and/or the composition of any one of technical solutions 7, 67, 69 and 78, and/or the method of any one of technical solutions 8 to 59, 70 to 77 and 79 in preparing the polymorph N of the compound of formula S of technical solution 80.

Technical solution 83: A method for preparing the polymorph N of the compound of formula S of technical solution 80, comprising the steps of: reacting a compound of formula A with a compound of formula IX under an alkaline condition to obtain a wet product, and subjecting the wet product to crystallization, purification, and drying to obtain the polymorph N of the compound of formula S.

Technical solution 84: The method of technical solution 83, wherein the solvent is selected from the group consisting of: DMSO, aqueous alkali metal hydroxide solution, aqueous methanol solution, aqueous ethanol solution and water.

Technical solution 85: A composition comprising posaconazole and a compound of formula X,

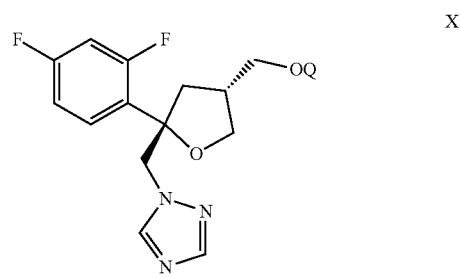

wherein, with respect to a total mass of the composition, a mass percentage of the compound of formula IX is 95% to 100%, and a mass percentage of the compound of formula X is 0% to 5.0%; and the posaconazole is preferably the polymorph N of technical solution 80 or 81.

In one aspect of the present invention, through the technical solutions of the present invention, intermediates IV and V can be obtained in a solid form, and the separation thereof is very convenient and efficient, such that intermediate VII of high purity can be prepared.

BRIEF DESCRIPTION OF DRAWINGS

FIG. 1 is an XRD spectrum of a polymorph N of a compound of formula S, in which: Peak position (34 peaks, maximal P/N=110.6)

Peak: 21-PTS/Parabola Filter, Threshold=3.0, Cut-Off=0.1%, BG=3/1.0, Peak-Top=The Highest Point

| 2-θ | d(A) | BG | Height | I % | Area | I % | FWHM |
|---|---|---|---|---|---|---|---|
| 6.001 | 14.7158 | 6110 | 4869 | 8.6 | 60867 | 8 | 0.213 |
| 7.82 | 11.2967 | 6980 | 15437 | 27.4 | 327843 | 43 | 0.361 |
| 9.779 | 9.0372 | 5929 | 3103 | 5.5 | 50433 | 6.6 | 0.276 |
| 11.759 | 7.5194 | 4856 | 41329 | 73.4 | 760347 | 99.7 | 0.313 |
| 13.739 | 6.44 | 4316 | 21174 | 37.6 | 431889 | 56.6 | 0.347 |
| 15.54 | 5.6976 | 4839 | 7859 | 14 | 132108 | 17.3 | 0.286 |
| 16.281 | 5.4397 | 5180 | 4570 | 8.1 | 51134 | 6.7 | 0.19 |
| 16.999 | 5.2115 | 5016 | 15251 | 27.1 | 207768 | 27.3 | 0.232 |
| 17.899 | 4.9514 | 5654 | 9263 | 16.5 | 130512 | 17.1 | 0.24 |
| 18.4 | 4.8179 | 5327 | 20874 | 37.1 | 318080 | 41.7 | 0.259 |
| 18.961 | 4.6764 | 6188 | 9622 | 17.1 | 114080 | 15 | 0.202 |
| 19.841 | 4.471 | 5675 | 4953 | 8.8 | 146668 | 19.2 | 0.503 |
| 20.16 | 4.4011 | 5685 | 7287 | 12.9 | 151648 | 19.9 | 0.354 |
| 21.579 | 4.1146 | 6177 | 35874 | 63.7 | 506732 | 66.5 | 0.24 |
| 22.96 | 3.8703 | 6795 | 11665 | 20.7 | 186034 | 24.4 | 0.271 |
| 24.518 | 3.6277 | 7821 | 2919 | 5.2 | 99013 | 13 | 0.577 |
| 25.039 | 3.5534 | 8471 | 56310 | 100 | 762407 | 100 | 0.23 |
| 25.72 | 3.4608 | 8457 | 4606 | 8.2 | 133577 | 17.5 | 0.493 |
| 26.078 | 3.4141 | 8001 | 10054 | 17.9 | 205987 | 27 | 0.348 |
| 26.8 | 3.3237 | 7059 | 4293 | 7.6 | 66117 | 8.7 | 0.262 |
| 27.68 | 3.2201 | 6438 | 8139 | 14.5 | 115050 | 15.1 | 0.24 |
| 28.8 | 3.0973 | 6255 | 3855 | 6.8 | 59693 | 7.8 | 0.263 |
| 29.419 | 3.0336 | 5946 | 2994 | 5.3 | 59722 | 7.8 | 0.339 |
| 29.92 | 2.9839 | 6060 | 1329 | 2.4 | 19706 | 2.6 | 0.252 |
| 31.199 | 2.8644 | 5243 | 2376 | 4.2 | 45823 | 6 | 0.328 |
| 32.119 | 2.7845 | 5171 | 965 | 1.7 | 14421 | 1.9 | 0.254 |
| 32.959 | 2.7154 | 4907 | 2356 | 4.2 | 30538 | 4 | 0.22 |
| 34.32 | 2.6107 | 4374 | 2708 | 4.8 | 58069 | 7.6 | 0.365 |
| 34.681 | 2.5844 | 4297 | 1829 | 3.2 | 37272 | 4.9 | 0.346 |
| 36.04 | 2.49 | 3962 | 1979 | 3.5 | 33757 | 4.4 | 0.29 |
| 36.619 | 2.452 | 4006 | 1634 | 2.9 | 18704 | 2.5 | 0.195 |
| 38.981 | 2.3087 | 3776 | 1423 | 2.5 | 13723 | 1.8 | 0.164 |
| 40.121 | 2.2456 | 3368 | 1189 | 2.1 | 31362 | 4.1 | 0.448 |
| 40.62 | 2.2192 | 3279 | 1449 | 2.6 | 40524 | 5.3 | 0.475 |

DETAILED DESCRIPTION

Terms used in the present invention have the following meanings.

The term "alkyl" as used herein represents a linear or branched saturated monovalent hydrocarbon radical.

The term "$C_1$-$C_4$ alkyl" as used herein represents a linear or branched saturated monovalent hydrocarbon radical containing 1 to 4 carbon atoms, and examples of $C_1$-$C_4$ alkyl include, but not limited to: methyl, ethyl, propyl, isopropyl, n-butyl, isobutyl and tert-butyl.

The term "alkoxy" as used herein represents an —O-alkyl group wherein the alkyl is as defined above, such as methoxy, ethoxy, n-propoxy, isopropoxy, n-butoxy, isobutoxy, t-butoxy, pentyloxy, and hexyloxy, including their isomers. The term "lower alkoxy" as used herein represents an alkoxy having the "lower alkyl" as defined above. The term "$C_{1-10}$ alkoxy" as used herein refers to an —O-alkyl group wherein the alkyl is $C_{1-10}$.

The term "haloalkyl" as used herein represents a linear or branched alkyl as defined above, wherein 1, 2, 3 or more hydrogen atoms are substituted by halogen. The term "lower haloalkyl" represents a linear or branched hydrocarbon radical containing 1 to 6 carbon atoms, wherein 1, 2, 3 or more hydrogen atoms are substituted by halogen. Examples include 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "aryl" as used herein represents a monovalent monocyclic or bicyclic aromatic hydrocarbyl group, preferably a 6- to 10-membered aromatic ring system. Preferred aryl includes, but not limited to phenyl, naphthyl, tolyl, and xylyl.

The term "substituted or unsubstituted" as used herein means being able to be substituted by one or more substituents selected from the group consisting of hydroxy, cyano, alkyl, alkoxy, thio groups, lower haloalkoxy, alkylthio, halogen, haloalkyl, alkylsulfinyl, alkylsulfonyl, halogen, amino, alkylamino, dialkylamino, aminoalkyl, alkylaminoalkyl, dialkylaminoalkyl, nitro, alkoxycarbonyl, carbamyl, alkylcarbamyl, dialkylcarbamyl, arylcarbamyl, alkylcarbonylamino, and arylcarbonylamino; preferably $C_1$-$C_4$ alkyl, alkoxy, or halogen.

A particular embodiment of the present invention provides a method for preparing a compound of formula IX, comprising the steps of:

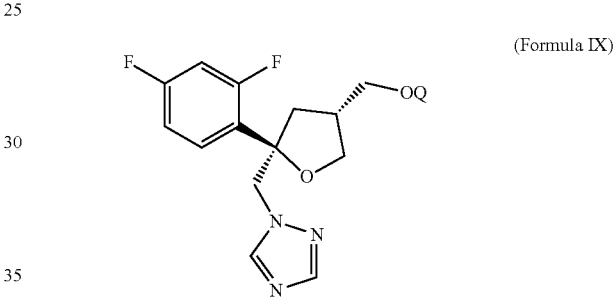

(Formula IX)

wherein Q is p-tosylsulfonyl, p-chlorophenylsulfonyl, or the like;

(1) subjecting a compound of formula I and a compound of formula II to an acylation reaction to produce a compound of formula III,

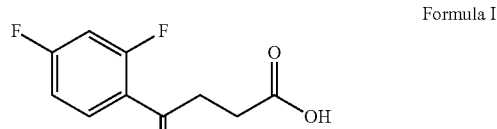

Formula I

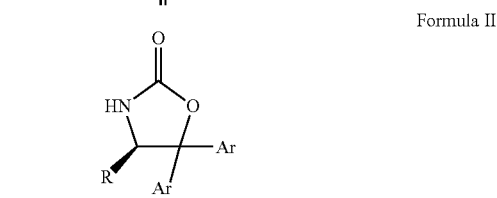

Formula II

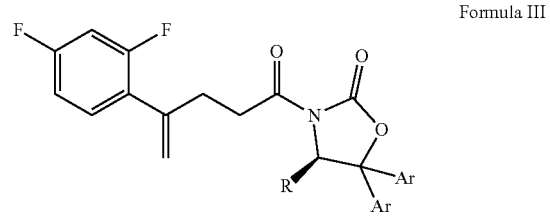

Formula III wherein R is selected from the group consisting of $C_1$-$C_4$ alkyl, phenyl or substituted phenyl, and benzyl or substituted benzyl, preferably isopropyl; and Ar is selected from phenyl or substituted phenyl, such as p-methoxyphenyl and the like;

(2) subjecting the compound of formula III to a hydroxy methylenation reaction with triformol under an action of an organic base and titanium tetrachloride to produce a compound of formula IV,

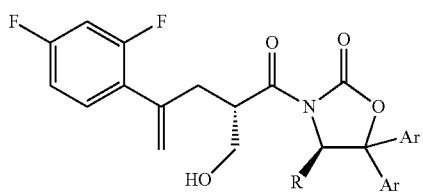

wherein R and Ar are as defined above;

(3) reacting the compound of formula IV with halogen or a halogenating agent in a suitable solvent under a neutral or alkaline condition to produce a compound of formula V,

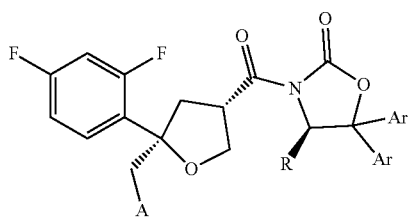

wherein A is selected from Cl, Br or I, preferably Br or I; and R and Ar are as defined above;

(4a) subjecting the compound of formula V to a hydrolyzation reaction in a suitable solvent under an alkaline condition to produce a compound of formula VI,

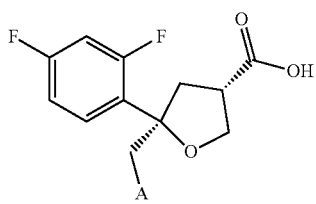

wherein A is as defined above;
or (4b) reacting the compound of formula V in a suitable solvent in the presence of a reducing agent to produce a compound of formula VII,

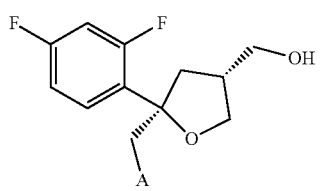

(5) reacting the compound of formula VI under a suitable reducing agent condition to produce a compound of formula VII,

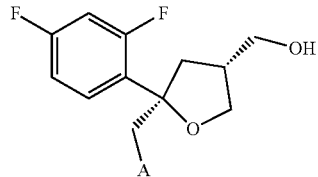

wherein A is as defined above;

(6) reacting the compound of formula VII with 1,2,3-triazole alkali metal salt or 1,2,3-triazole in the presence of a base, a suitable reaction solvent and a catalyst to produce a compound of formula VIII,

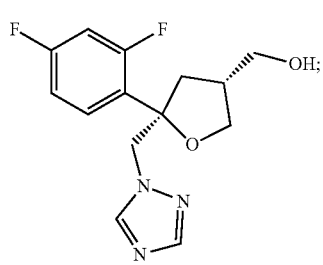

and
(7) reacting the compound of formula VIII with QX sulfonyl compound to produce a compound of formula IX,

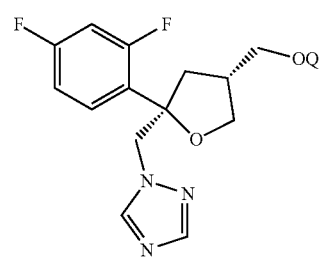

wherein Q is selected from the group consisting of p-tosylsulfonyl, p-chlorophenylsulfonyl, and the like.

Here, in step (1), the acylating agent used in the acylation reaction may be selected from the group consisting of oxalyl chloride, pivaloyl chloride, thionyl chloride, $POCl_3$, $PCl_3$, and $PCl_5$, preferably oxalyl chloride or pivaloyl chloride; the base is selected from the group consisting of organometallic reagents such as butyl lithium and lithium diisopropylamide, or a mixture of an organic tertiary amine, such as triethylamine, diisopropylethylamine, pyridine, 4-dimethylaminopyridine, and N-methylmorpholine, and anhydrous lithium chloride; it is preferable to use an acylation condition where the acylating agent is oxalyl chloride or thionyl chloride, and the base is butyl lithium, and an acylation condition where the acylating agent is pivaloyl chloride, and the base is triethylamine and anhydrous lithium chloride; and the solvent is selected from the group consisting of one of polar aprotic solvents such as a chlorine-containing solvent and an ether solvent, preferably tetrahydrofuran or dichloromethane, or a mixed solvent of more than one of them.

In step (2), the organic base is selected from the group consisting of organic tertiary amines, such as triethylamine, tri(tert-butyl)amine, N-methylmorpholine, diisopropylethylamine, and the like, preferably triethylamine or diisopropylethylamine; and the solvent is selected from the group consisting of aprotic solvents such as a chlorine-containing solvent, an ester solvent, and an ether solvent, preferably dichloromethane or 1,2-dichloroethane.

In step (3), the halogenating agent includes halogen, dihalo-hydantoin, N-bromosuccinimide (NBS), N-iodosuccinimide (NIS), N-chlorosuccinimide (NCS), and the like, preferably iodine, NIS bromine, NBS or dibromo-hydantoin; the base is selected from the group consisting of alkali metal hydroxides, metal carbonates, and metal bicarbonates, preferably sodium bicarbonate; and the solvent is selected from the group consisting of one of polar aprotic solvents such as tetrahydrofuran, acetonitrile, and ethyl acetate, and protic solvents such as water and alcohol solvents, or a mixed solvent of more than one of them, preferably a mixture of tetrahydrofuran and water.

In step (4a), the base is selected from the group consisting of alkali metal hydroxides, and metal carbonates, preferably sodium hydroxide; and the solvent is selected from the group consisting of a mixture of an organic polar protic or aprotic solvent and water, preferably tetrahydrofuran and water.

In step (4b), the reducing agent is selected from the group consisting of hydride reducing agents, preferably lithium borohydride; the solvent is selected from the group consisting of methanol, ethanol, isopropanol, tetrahydrofuran, 2-methyltetrahydrofuran, dichloromethane and ethyl acetate, or a mixed solvent of more than one of them.

In step (5), the reducing agent is selected from the group consisting of diisobutylaluminum hydride, sodium borohydride, lithium borohydride, sodium borohydride/BF$_3$-diethyl ether, sodium aluminum bis(dihydride), sodium borohydride/aluminum chloride or borane/aluminum chloride, sodium borohydride/iodine, 9-BNN, and vitride solution; and the solvent is selected from the group consisting of organic polar aprotic solvents, such as tetrahydrofuran, toluene, and dichloromethane, preferably tetrahydrofuran or toluene.

In step (6), the base may be selected from the group consisting of metal hydrides, metal alkoxides, and metal carbonates, such as NaH, KH, sodium alkoxide, Na$_2$CO$_3$, and K$_2$CO$_3$; the catalyst includes crown ethers, such as 15-crown-5 and 18-crown-6; and the reaction solvent may be selected from the group consisting of dipolar aprotic solvents, such as dimethylsulfoxide, N,N-dimethylformamide, N,N-dimethylacetamide, and N-methylpyrrolidinone.

A particular embodiment of the present invention provides a method for preparing a compound of formula IX, comprising the steps of:

(1) subjecting a compound of formula V-a to a hydrolyzation reaction in a suitable solvent under an alkaline condition to produce a compound of formula VI-a,

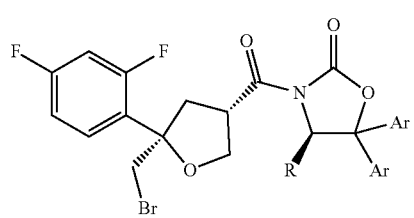

V-a

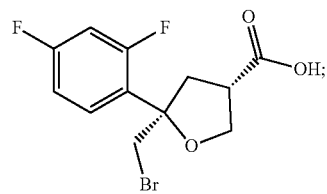

VI-a (2) reacting the compound of formula VI-a under a suitable reducing agent condition to produce a compound of formula VII-a,

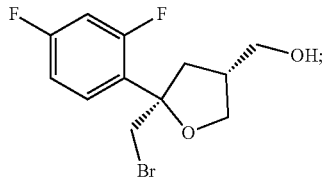

VII-a (3) reacting the compound of formula VII-a with 1,2,3-triazole alkali metal salt or 1,2,3-triazole in the presence of a base, a suitable reaction solvent and a catalyst to produce a compound of formula VIII,

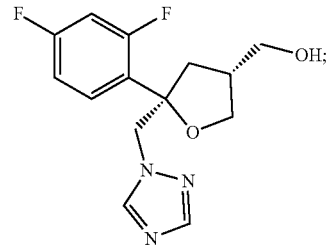

VIII and (4) reacting the compound of formula VIII with QX sulfonyl compound to produce a compound of formula IX,

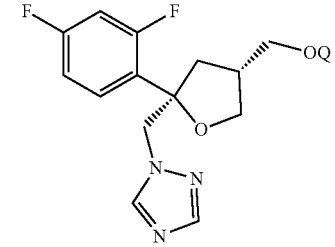

IX wherein Q is selected from the group consisting of tosylsulfonyl, p-chlorophenylsulfonyl, and the like.

Here, in step (1), the base is selected from the group consisting of alkali metal hydroxides, and metal carbonates, preferably sodium hydroxide; and the solvent is selected from the group consisting of a mixture of an organic polar protic or aprotic solvent and water, preferably tetrahydrofuran and water.

In step (2), the reducing agent is selected from the group consisting of diisobutylaluminum hydride, sodium borohydride, lithium borohydride, sodium borohydride/BF$_3$-diethyl ether, sodium aluminum bis(dihydride), sodium borohydride/aluminum chloride or borane/aluminum chloride, sodium borohydride/iodine, 9-BNN, and vitride solution; and the solvent is selected from the group consisting of organic polar aprotic solvents, such as tetrahydrofuran, toluene, and dichloromethane, preferably tetrahydrofuran or toluene.

In step (3), the base may be selected from the group consisting of metal hydrides, metal alkoxides, and metal carbonates, such as NaH, KH, sodium alkoxide, Na$_2$CO$_3$, and K$_2$CO$_3$; the catalyst includes crown ethers, such as 15-crown-5 and 18-crown-6; and the reaction solvent may be selected from the group consisting of dipolar aprotic solvents, such as dimethylsulfoxide, N,N-dimethylformamide, N,N-dimethylacetamide, and N-methylpyrrolidinone.

In step (4), the base is selected from the group consisting of organic bases, such as triethylamine, tributylamine, 4-dimethylaminopyridine, N-methylmorpholine, and diisopropylethylamine, preferably diisopropylethylamine; and the solvent is selected from the group consisting of alcohol solvents, chlorinated solvents and hydrocarbon solvents, preferably petroleum ether, isopropanol, or dichloromethane.

The present invention provides a method for preparing a compound of formula IV, comprising the steps of:

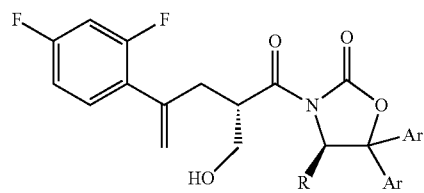

IV (1) subjecting a compound of formula I and a compound of formula II to an acylation reaction to produce a compound of formula III,

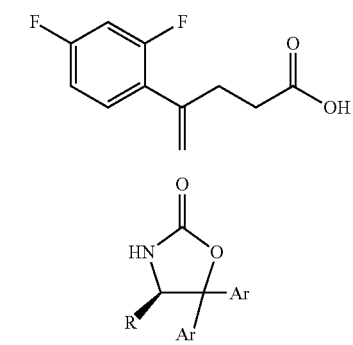

Formula I

Formula II

Formula III wherein R and Ar are as defined above; and (2) subjecting the compound of formula III to a hydroxy methylenation reaction with triformol under an action of an organic base and titanium tetrachloride to produce a compound of formula IV.

Alternatively, the compound of formula IV is synthesized by using the compound of formula III as a starting material.

An embodiment of the present invention provides a method for preparing a compound of formula VI, comprising the steps of:

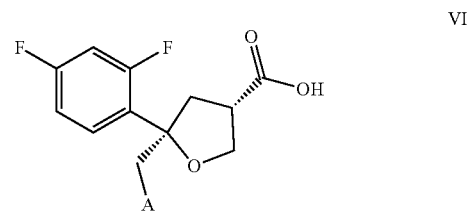

VI wherein A is selected from Cl, Br or I, preferably Br or I;

(1) subjecting a compound of formula I and a compound of formula II to an acylation reaction to produce a compound of formula III,

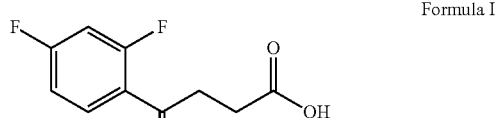

Formula I

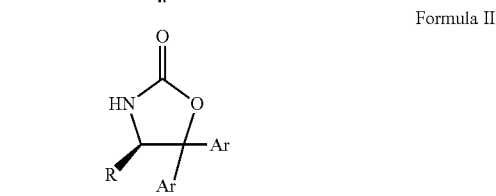

Formula II

Formula III wherein R and Ar are as defined above;

(2) subjecting the compound of formula III to a hydroxy methylenation reaction with triformol under an action of an organic base and titanium tetrachloride to produce a compound of formula IV,

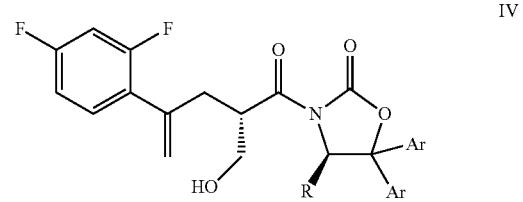

IV wherein R and Ar are as defined above;

(3) reacting the compound of formula IV with halogen or a halogenating agent in a suitable solvent under a neutral or alkaline condition to produce a compound of formula V,

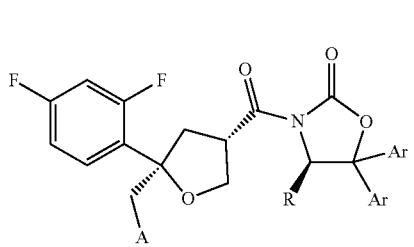

wherein A is as defined above; and R and Ar are as defined above; and (4) subjecting the compound of formula V to a hydrolyzation reaction in a suitable solvent under an alkaline condition to produce a compound of formula VI.

The present invention provides intermediate compounds of formula III and formula IV, and their use in synthesizing a compound of formula IX,

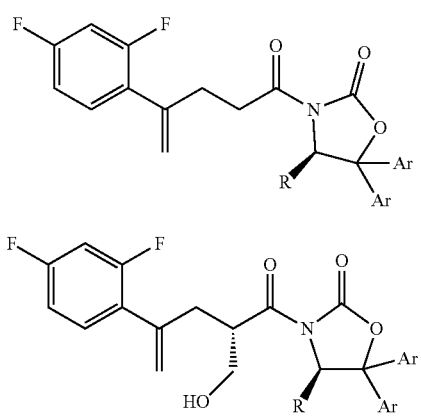

wherein R is selected from the group consisting of $C_1$-$C_4$ alkyl, phenyl or substituted phenyl, and benzyl or substituted benzyl, preferably isopropyl; and Ar is selected from the group consisting of phenyl or substituted phenyl, such as p-methoxyphenyl and the like.

The present invention provides intermediate compounds of formula III and formula IV in a solid form.

The present invention provides an intermediate compound of formula V, and its use in synthesizing a compound of formula IX and posaconazole,

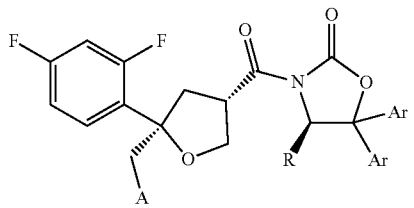

wherein A is selected from Cl, Br or I, preferably Br or I; R is selected from the group consisting of C1-C4 alkyl, phenyl or substituted phenyl, and benzyl or substituted benzyl, preferably isopropyl; and Ar is selected from the group consisting of phenyl or substituted phenyl, such as p-methoxyphenyl and the like.

The present invention provides an intermediate compound of formula VI-a, and its use in synthesizing a compound of formula IX and posaconazole,

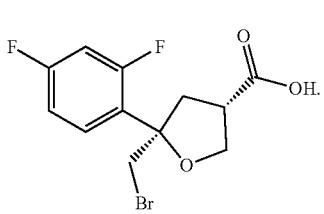

Various aspects and characteristics of the present invention will be further described below.

The abbreviations as used herein are generally well-known to those skilled in the art, or can be understood easily according to fundamental knowledge.

The starting materials used in the preparation of the compound of the present invention are known, can be prepared according to a known method, or are commercially available.

The present invention also relates to new intermediates and/or starting materials. Reaction conditions and new intermediates the same as or similar to those mentioned in the embodiments are particularly preferred.

All the intermediates and final products can be post-treated and/or purified according to conventional methods, which include pH adjustment, extraction, filtration, drying, concentration, chromatography, grinding, crystallization and the like.

Further, the compound of the present invention may also be prepared by various methods known in the art or a variant of the method described herein.

The following examples are only intended to illustrate the present invention, but not to limit the present invention in any manner.

(1) Preparation of the Compound of Formula III 2.5 g (1.2 mmol) of compound of formula I and 3.45 ml (2.5 mmol) TEA were added to 25 ml THF. The mixture was cooled to −20° C. 1.4 ml (1.2 mmol) pivaloyl chloride was dropwise added thereto. The mixture was stirred and reacted for 2 h with the temperature kept at −20° C., and then warmed up to room temperature. 2.81 g (1.0 mmol) of compound of formula II and 0.5 g (1.1 mmol) anhydrous lithium chloride were sequentially added thereto. The mixture was stirred at room temperature for 24 h. Tetrahydrofuran was removed by reduced pressure distillation on the next day. Water was added to the residue. The mixture was extracted with methyl tert-butyl ether twice. The ether extract liquors were combined, washed sequentially with saturated NaHCO$_3$ solution, 1 N HCl, water, and saturated NaCl solution, dried over anhydrous Na$_2$SO$_4$, and filtered. The filtrate was evaporated to dryness. The residue was recrystallized with n-hexane to obtain 3.52 g of colorless crystal (63%).

(2) Preparation of the Compound of Formula IV 1.5 g (3.15 mmol) of compound of formula III was cooled in an ice/salt bath. Then, 3.3 ml of 1N TiCl$_4$/DCM solution was dropwise added thereto. After that, the mixture was stirred for 15 min. 0.46 ml (3.3 mmol) was dropwise added thereto. The mixture was stirred for 30 min. Then, 0.3 g (3.3 mmol) triformol/1 ml DCM solution was dropwise added thereto. After that, 3.3 ml of 1N TiCl$_4$/DCM solution was dropwise added thereto. After that, the mixture was stirred and reacted in an ice bath for 3 h, and 20 ml half-saturated NH$_4$Cl was added thereto to stop the reaction. The mixture was stirred at RT for 15 min. Tert-butyl methyl ether was added thereto for dilution. The organic layer was separated, washed sequentially with 1N HCl, saturated NaHCO$_3$ solution, and saturated NaCl solution, dried over Na$_2$SO$_4$, and evaporated to dryness under a reduced pressure, to obtain 1.6 g of off-white solid.

$^1$HNMR (400 MHz, CDCl$_3$) δ 7.20~7.52 (m, 11H), 6.72~6.68 (m, 1H), 6.64~6.60 (t, J=8 Hz, 1H), 6.64~6.52 (m, 1H), 5.42 (s, 1H), 4.86 (s, 1H), 4.73 (s, 1H), 3.90~3.96 (m, 1H), 3.82~3.86 (dd, J=10.8, 4.4 Hz, 1H), 3.71~3.76 (m, 1H), 2.63~2.90 (dd, j=14, 8.8 Hz, 1H), 2.43~2.48 (dd, J=14, 5.2, 1H), 1.92~2.0 (m, 1H), 0.88~0.90 (d, J=6.8, 3H), 0.76~0.77 (d, J=6.8, 3H) Product; $[\alpha]_D^{20}$; +131.9 (CHCl$_3$, C 0.48)

(3) Preparation of the Compound of Formula V 250 mg (0.5 mmol) starting material was added to 5 ml THF and 0.2 ml H2O. The mixture was cooled in an ice/salt bath. Then, 106 mg (0.6 mol) NBS was added thereto. After that, the mixture was stirred and reacted in an ice bath for 2.5 h. 20 ml tert-butyl methyl ether was added thereto for dilution. The mixture was washed sequentially with saturated sodium bisulfite solution, water, and saturated NaCl solution, dried over Na$_2$SO$_4$, and filtered. The filtrate was concentrated, then purified by a silica gel short column to remove impurities at the origin, and eluted with PL/EtOAc, to obtain 240 mg of white solid.

$^1$HNMR (400 MHz, CDCl$_3$) δ 7.28~7.51 (m, 11H), 6.85~6.89 (m, 1H), 6.75~6.80 (m, 1H), 5.38 (s, 1H), 4.30 (s, 1H), 4.28 (s, 1H), 3.95~3.98 (m, 1H), 3.73~3.76 (d, J=11.2 Hz, 1H), 3.68~3.71 (d, J=11.2 Hz, 1H), 2.50~2.55 (m, 1H), 2.34~2.40 (m, 1H), 1.98~2.04 (m, 1H), 0.88~0.90 (d, J=6.8, 3H), 0.75~0.77 (d, J=6.8, 3H). $[\alpha]_D^{20}$; +112.2 (CHCl$_3$, C 0.505)

(4) Preparation of the Compound of Formula VI 160 mg starting material was dissolved in 2.5 ml MeOH and 2.5 ml THF 0.43 ml of 1M NaOH was added thereto. The mixture was stirred and reacted at room temperature for 2 h. The solvent was removed by reduced pressure distillation. 15 ml H$_2$O was added to the residue. The auxiliary was filtered and recovered. The filtrate was adjusted to about pH 2 with concentrated hydrochloric acid, and extracted with EtOAc twice. The extract liquors were combined, washed with water, dried over Na$_2$SO$_4$, and filtered. The filtrate was evaporated to dryness, purified by a silica gel short column, and eluted with PL/EtOAc (1/1), to obtain 85 mg of oil, which was left standing for solidification.

$^1$HNMR (400 MHz, CDCl$_3$) δ 7.49~7.55 (m, 1H), 6.87~6.92 (m, 1H), 6.80~6.85 (m, 1H), 4.28~4.32 (t, J=8.8 Hz, 1H), 4.16~4.21 (t, J=8.8 Hz, 1H), 3.82~3.85 (d, J=10.8 Hz, 1H), 3.77~3.80 (d, J=10.8 Hz, 1H), 3.11~3.15 (m, 1H), 2.74~2.79 (m, 1H), 2.62~2.67 (m, 1H)

(5) Preparation of the Compound of Formula VII

The starting material was dissolved in 3 ml THF, and cooled in an ice bath. 0.05 ml BH$_3$.S(Me)$_2$ was added thereto. After that, the mixture was stirred and reacted in an ice bath for 15 min, stirred at room temperature for 35 min, and methanol was added thereto to stop the reaction. The solvent was removed by reduced pressure distillation. Tert-butyl methyl ether was added to the residue. The mixture was washed with saturated NaHCO$_3$ solution and water, dried over Na$_2$SO$_4$, and filtered. The filtrate was concentrated, then purified by a silica gel short column, and eluted with PL/EtOAc (2/1), to obtain an oil.

$^1$HNMR (400 MHz, CDCl$_3$) δ 7.51~7.57 (m, 1H), 6.87~6.90 (m, 1H), 6.78~6.80 (m, 1H), 4.09~4.11 (dd, J=7.0, 4.2 Hz, 1H), 3.87~3.91 (dd, J=7.0, 4.2 Hz, 1H), 3.79 (s, 2H), 3.70~3.72 (m, 2H), 2.42~2.51 (m, 2H), 2.15~2.19 (m, 1H), 1.49 (brs, 1H) $[\alpha]_D^{20}$; +2.3 (CHCl$_3$, C 0.98)

(6) Preparation of the Compound of Formula VIII 165 mg starting material was dissolved in 2.5 ml DMSO. 290 mg triazole sodium, 50 mg NaI and 1 d 15-crown-5 were added thereto. The mixture was heated, stirred and reacted in an oil bath at 80~90° C. for 24 h. Methyl-THF was added for dilution. The mixture was washed with water three times and with saturated NaCl solution, dried over Na$_2$SO$_4$, and filtered. The filtrate was concentrated, and then purified by a silica gel short column, and eluted with DCM~DCM/MeOH (10/1), to obtain 100 mg of product. HR-MS (ESI) C$_{14}$H$_{16}$F$_2$N$_3$O$_2$ (M+H)+: calcd. 296.1205, found 296.1200.

(7) Preparation of the Compound of Formula IX 310 mg (1.05 mmol) starting material was dissolved in 5 ml DCM. 0.36 ml (2.5 mmol) Et$_3$N and 64 mg DMAP were added thereto. The mixture was cooled in an ice bath. 220 mg (1.1 mmol) TsCl was added thereto. After that, the mixture was reacted in an ice bath for 30 min, displaced to an environment at room temperature (about 15° C.), and stirred and reacted overnight. The reaction liquid was diluted with DCM, washed sequentially with 1 N HCl, saturated NaHCO$_3$ solution, and water, dried over Na$_2$SO$_4$, and filtered. The filtrate was evaporated to dryness to obtain 370 mg of pale yellow gum (entraining solid), which was then filled into a silica gel column and eluted with hexane/acetone (4/1~2/1), to obtain 210 mg of cis-product (white solid). Cis-product; $[\alpha]_D^{20}$=−37.4 (CHCl$_3$, C 1.0)

$^1$HNMR (400 MHz, CDCl$_3$) δ 8.02 (s, 1H), 7.74~7.76 (m, 3H), 7.35~7.37 (d, 2H), 7.3 (m, 1H), 6.80~6.83 (m, 2H), 4.43~4.55 (Abq, 2H), 3.96~4.00 (m, 1H), 3.82~3.86 (m, 1H), 3.66~3.71 (m, 1H), 3.55~3.58 (m, 1H), 2.48~2.51 (m, 2H), 2.47 (s, 3H), 1.89~1.92 (m, 1H) HR-MS (ESI) C21H22F2N3O4S (M+H)+: calcd. 450.1293, found 450.2414.

(8) Preparation of the Compound of Formula B 10 g of compound of formula A and 76 mL DMSO were added into a reaction flask at room temperature, and stirred until clarification. An alkaline solution previously prepared from 1.4 g sodium hydroxide and 6 g water was further added thereto. The mixture was stirred for 1 h. Then, 10 g of compound of formula IX was added thereto. The mixture was warmed up to 38° C. and reacted for 16 h. After the reaction was completed, the mixture was warmed up to 45° C. 6 mL water was added thereto. The mixture was stirred for 30-60 min. 154 mL water was further added thereto. The mixture was stirred for 1 h, and filtered under suction. The resultant solid was drip washed with 4×50 mL purified water to obtain a wet product.

The wet product and 60 mL of 90% aqueous ethanol solution were added to a reaction flask, warmed up to 65° C., and stirred. After clarification, 1.5 g active carbon was added thereto. The mixture was stirred for 15 min, filter-pressed while hot, and washed with 15 mL of 90% aqueous ethanol solution. Then, the filtrate was warmed up to 65° C., stirred, cooled to 40-45° C. after clarification, crystallized while keeping the temperature for 1 h, further cooled to 0-5° C., crystallized while keeping the temperature for 1 h, and filtered under suction. The resultant solid was first drip washed with 5 mL of 50% aqueous ethanol solution, and then drip washed with 4×50 mL purified water. The solid was collected, placed in a ventilated oven at 50-55° C. and dried for 16 h to obtain 13.2 g of product.

(9) Preparation of Posaconazole 10 g of compound of formula B, 100 mL methanol and 10 g refined hydrochloric acid were added to a reaction flask at room temperature, and stirred for 1 h. Then, 1 g of 5% Pd/C was added thereto. Then, hydrogen was introduced thereto. The mixture was warmed up to 40° C., and stirred and reacted for 10-16 h. After the reaction was completed, the mixture was filtered under suction. The resultant solid was washed with 10 mL methanol. The filtrate was warmed up to 45° C. And an alkaline solution prepared from 2.7 g sodium hydroxide and 17 g water was dropwise added thereto to adjust the pH of the solution to 7-8. Then, the mixture was warmed up to 60-65° C. And 60 mL purified water was slowly dropwise added thereto. After that, the mixture was cooled to 45° C., crystallized while keeping the temperature for 1 h, further cooled to 15-20° C., crystallized while keeping the temperature for 1 h, and filtered under suction. The resultant solid was first drip washed with 5 mL of 50% aqueous methanol solution, and then drip washed with 4×50 mL purified water. The solid was collected, placed in a ventilated oven at 50-55° C. and dried for 16 h to obtain 9.4 g of product.

For the purpose of clarity and easy understanding, the above invention has been described in detail through illustration and embodiments. It is apparent for those skilled in the art that changes and modifications can be made within the scopes of the appended claims. Therefore, it should be understood that the above description is intended for illustration, but not limitation. Therefore, the scope of the present invention should not be defined according to the above description, but according to all scopes of the appended claims and the equivalents thereof.

What is claimed is:

1. A compound of formula III,

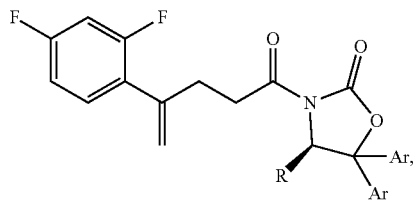

Formula III wherein,

R is selected from the group consisting of $C_1$-$C_4$ alkyl, substituted or unsubstituted phenyl, and substituted or unsubstituted benzyl; and two Ar groups are the same or different, and are each independently selected from the group consisting of substituted or unsubstituted aryl groups, wherein the compound is in a solid form.

2. A compound of formula IV,

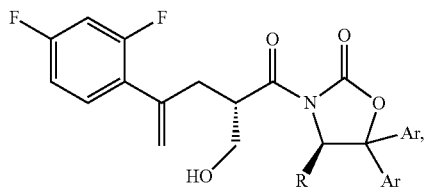

IV wherein,

R is selected from the group consisting of $C_1$-$C_4$ alkyl, substituted or unsubstituted phenyl, and substituted or unsubstituted benzyl; and two Ar groups are the same or different, and are each independently selected from the group consisting of substituted or unsubstituted aryl groups, wherein the compound is in a solid form.

3. A compound of formula V,

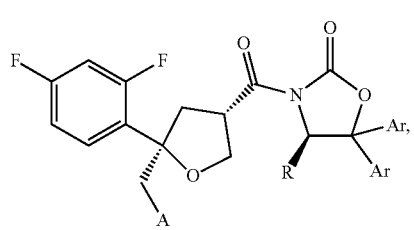

V wherein,

R is selected from the group consisting of $C_1$-$C_4$ alkyl, substituted or unsubstituted phenyl, and substituted or unsubstituted benzyl, two Ar groups are the same or different, and are each independently selected from the group consisting of substituted or unsubstituted aryl groups, and A is Br, Cl or I, wherein the compound is in a solid form.

4. A method for preparing a compound of formula V,

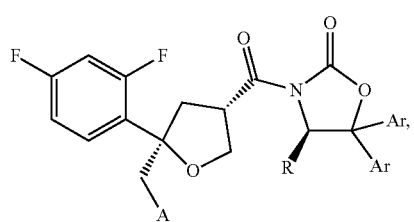

V comprising:

step 1) subjecting a compound of formula I and a compound of formula II to an acylation reaction,

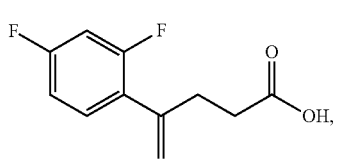

Formula I

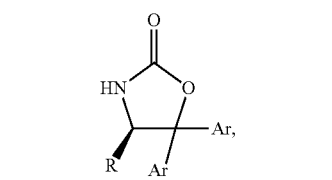

Formula II to obtain a compound of formula III,

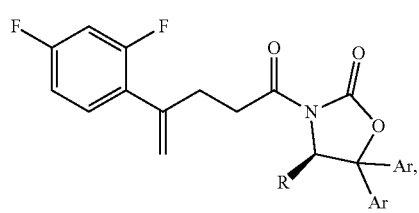

Formula III step 2) subjecting the compound of formula III to a hydroxyl methylenation with triformol to obtain a compound of formula IV,

IV and step 3) reacting the compound of formula IV with a halogenating agent, wherein, R is selected from the group consisting of $C_1$-$C_4$ alkyl, substituted or unsubstituted phenyl, and substituted or unsubstituted benzyl, two Ar groups are the same or different, and are each independently selected from the group consisting of substituted or unsubstituted aryl groups, and A is Br, Cl or I.

5. The method of claim 4, wherein, in step 3), the reaction is carried out under a neutral or alkaline condition; and/or the halogenating agent comprises one or more selected from the group consisting of halogen, dihalo-hydantoin, N-bromosuccinimide (NBS), N-iodosuccinimide (NIS), and N-chlorosuccinimide (NCS); and/or the reaction is carried out in the presence of one or more bases selected from the group consisting of alkali metal hydroxides, metal carbonates, and metal bicarbonates; and/or the reaction is carried out in one or more solvents selected from the group consisting of polar aprotic solvents, and protic solvents.

6. A method for synthesizing posaconazole, comprising:

Step 1-a-1) hydrolyzing a compound of formula V,

V to obtain a compound of formula VI,

VI and step 1-a-2) reducing the compound of formula VI to obtain a compound of formula VII,

VII or step 1-b) reducing a compound of formula V,

V to obtain a compound of formula VII,

VII step 2) reacting the compound of formula VII with 1,2,3-triazole alkali metal salt or 1,2,3-triazole to obtain a compound of formula VIII,

VIII step 3) sulfonylating the compound of formula VIII to obtain a compound of formula IX,

IX step 4) reacting the compound of formula IX with a compound of formula A,

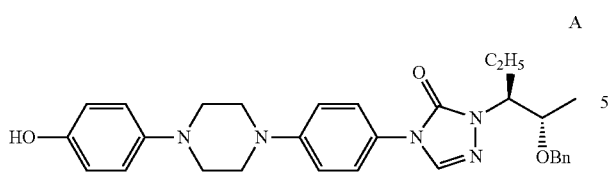

to obtain a compound of formula B,

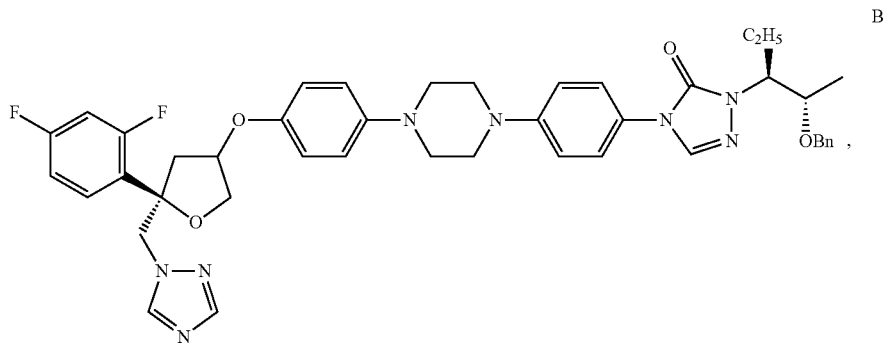 [SMILES: CC[C@@H]([C@H](C)OCc1ccccc1)n1ncn(-c2ccc(N3CCN(c4ccc(OC5CO[C@@](Cn6cncn6)(c6ccc(F)cc6F)C5)cc4)CC3)cc2)c1=O]

and hydrolyzing the compound of formula B into posaconazole, wherein,

R is selected from the group consisting of $C_1$-$C_4$ alkyl, substituted or unsubstituted phenyl, and substituted or unsubstituted benzyl, two Ar groups are the same or different, and are each independently selected from the group consisting of substituted or unsubstituted aryl groups, A is Br, Cl or I, and Q is selected from substituted or unsubstituted phenylsulfonyl.

7. A polymorph N of a compound of formula B,

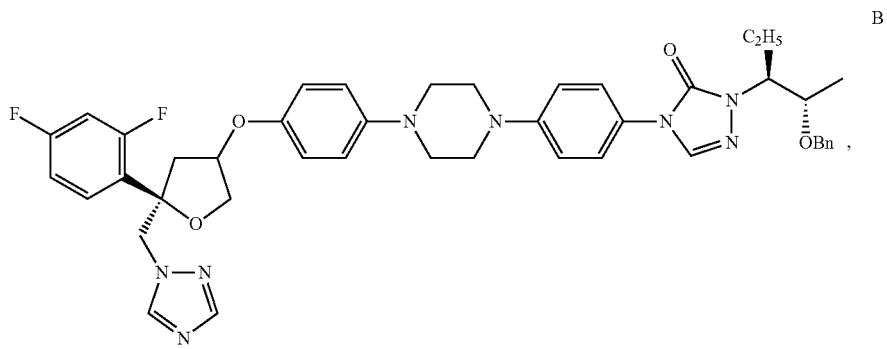 [SMILES: CC[C@@H]([C@H](C)OCc1ccccc1)n1ncn(-c2ccc(N3CCN(c4ccc(OC5CO[C@@](Cn6cncn6)(c6ccc(F)cc6F)C5)cc4)CC3)cc2)c1=O]

wherein the polymorph N has an XRD spectrum as shown in FIG. 1.

8. The method of claim 4, wherein, in step 1), one or more acylating agents selected from the group consisting of oxalyl chloride, pivaloyl chloride, thionyl chloride, $POCl_3$, $PCl_3$, and $PCl_5$ are used in the acylation reaction; and/or the acylation reaction is carried out in the presence of one or more bases selected from the group consisting of organometallic reagents, or a mixture of an organic tertiary amine and anhydrous lithium chloride; and/or the acylation reaction is carried out in the presence of a polar aprotic solvent.

9. The method of claim 8, wherein, the acylation reaction is carried out in the presence of butyl lithium, or pivaloyl chloride and a mixture of triethylamine and anhydrous lithium chloride.

10. The method of claim 4, wherein, in step 2), the hydroxy methylenation is carried out under an action of an organic base and titanium tetrachloride; and/or the organic base is one or more selected from the group consisting of organic tertiary amines; and/or the hydroxy methylenation is carried out in one or more solvents selected from the group consisting of aprotic solvents.

11. The method of claim 6, wherein, in step 1-a-1), the hydrolyzation is carried out under an alkaline condition; and/or the hydrolyzation is carried out in the presence of one or more bases selected from the group consisting of alkali metal hydroxides and metal carbonates; and/or the hydrolyzation is carried out in one or more solvents selected from the group consisting of a mixture of an organic polar protic or aprotic solvent and water.

12. The method of claim 6, wherein, in step 1-a-2), one or more reducing agents selected from the group consisting of diisobutylaluminum hydride, sodium borohydride, lithium borohydride, sodium borohydride/$BF_3$-diethyl ether, sodium aluminum bis(dihydride), sodium borohydride/aluminum chloride or borane/aluminum chloride, sodium borohydride/iodine and vitride solution are used in the reduction; and/or the reduction is carried out in one or more solvents selected from the group consisting of organic polar aprotic solvents.

13. The method of claim 6, wherein, in step 1-b),

One or more reducing agents selected from the group consisting of hydride reducing agents are used in the reduction-hydrogenation; and/or the reduction is carried out in one or more solvents selected from the group consisting of methanol, ethanol, isopropanol, tetrahydrofuran, 2-methyltetrahydrofuran, dichloromethane and ethyl acetate.

14. The method of claim 6, wherein, step 2) is carried out in the presence of one or more bases selected from the group consisting of metal hydroxides, metal alkoxides, and metal carbonates; and/or when A is Cl or Br, step 2) is carried out in the presence of one or more catalysts selected from the group consisting of crown ethers, tetrabutylammonium iodide, a catalytic amount of KI or NaI; and/or step 2) is carried out in one or more solvents selected from the group consisting of dipolar aprotic solvents.

15. The method of claim 6, wherein QX is used as a sulfonylating agent for the sulfonylation, wherein, Q is selected from substituted or unsubstituted phenylsulfonyl;

X is Br, Cl or I; and/or the sulfonylation is carried out in the presence of one or more bases selected from the group consisting of organic bases; and/or the sulfonylation is carried out in one or more solvents selected from the group consisting of chlorinated solvents and hydrocarbon solvents.

* * * * *